(12) United States Patent
Langer et al.

(10) Patent No.: US 8,203,006 B2
(45) Date of Patent: Jun. 19, 2012

(54) PROCESS FOR PRODUCING VINYLENE CARBONATE

(75) Inventors: Reinhard Langer, Tönisvorst (DE); Anke Beckmann, Köln (DE); Andreas Schulze Tilling, Leichlingen (DE); Paul Wagner, Düsseldorf (DE); Leslaw Mleczko, Dormagen (DE); Sigurd Buchholz, Köln (DE)

(73) Assignee: Saltigo GmbH, Langenfeld, DE (US)

( * ) Notice: Subject to any disclaimer, the term of this patent is extended or adjusted under 35 U.S.C. 154(b) by 652 days.

(21) Appl. No.: 11/920,040

(22) PCT Filed: May 4, 2006

(86) PCT No.: PCT/EP2006/004155
§ 371 (c)(1),
(2), (4) Date: Jul. 14, 2008

(87) PCT Pub. No.: WO2006/119909
PCT Pub. Date: Nov. 16, 2006

(65) Prior Publication Data
US 2009/0176997 A1    Jul. 9, 2009

(30) Foreign Application Priority Data
May 12, 2005  (DE) .................. 10 2005 021 964

(51) Int. Cl.
*C07D 317/40* (2006.01)
(52) U.S. Cl. .................................... 549/230
(58) Field of Classification Search ............. 549/230
See application file for complete search history.

(56) References Cited

U.S. PATENT DOCUMENTS
6,395,908 B1    5/2002  Seifert et al. ................ 549/229

FOREIGN PATENT DOCUMENTS
| DE | 1 135 452 | * | 8/1962 |
| GB | 957003 | | 4/1964 |
| JP | 2000/026449 | | 1/2000 |

OTHER PUBLICATIONS

Newman, M. and Addor, R., "Vinylene Carbonate", *J. Am. Chem. Soc.*, 1953, pp. 1263-1264.
Newman, M. and Addor, R., "Synthesis and Reactions of Vinylene Carbonate", *J. Am. Chem. Soc.*, 1955, pp. 3789-3793.
Johnson, W. K. and Patton, T. L.; "Preparation of Vinylene Carbonate", *J. Org. Chem.*, 1960, pp. 1042-1043.

* cited by examiner

*Primary Examiner* — Bernard Dentz
(74) *Attorney, Agent, or Firm* — Michael A. Miller

(57) ABSTRACT

The present invention relates to the industrial production of vinylene carbonate (VC) by eliminating hydrogen chloride from chloroethylene glycol carbonate (CGC) or solid catalysts in the gas phase, the reaction being carried out over a catalyst bed agitated by thorough mixing.

7 Claims, 1 Drawing Sheet

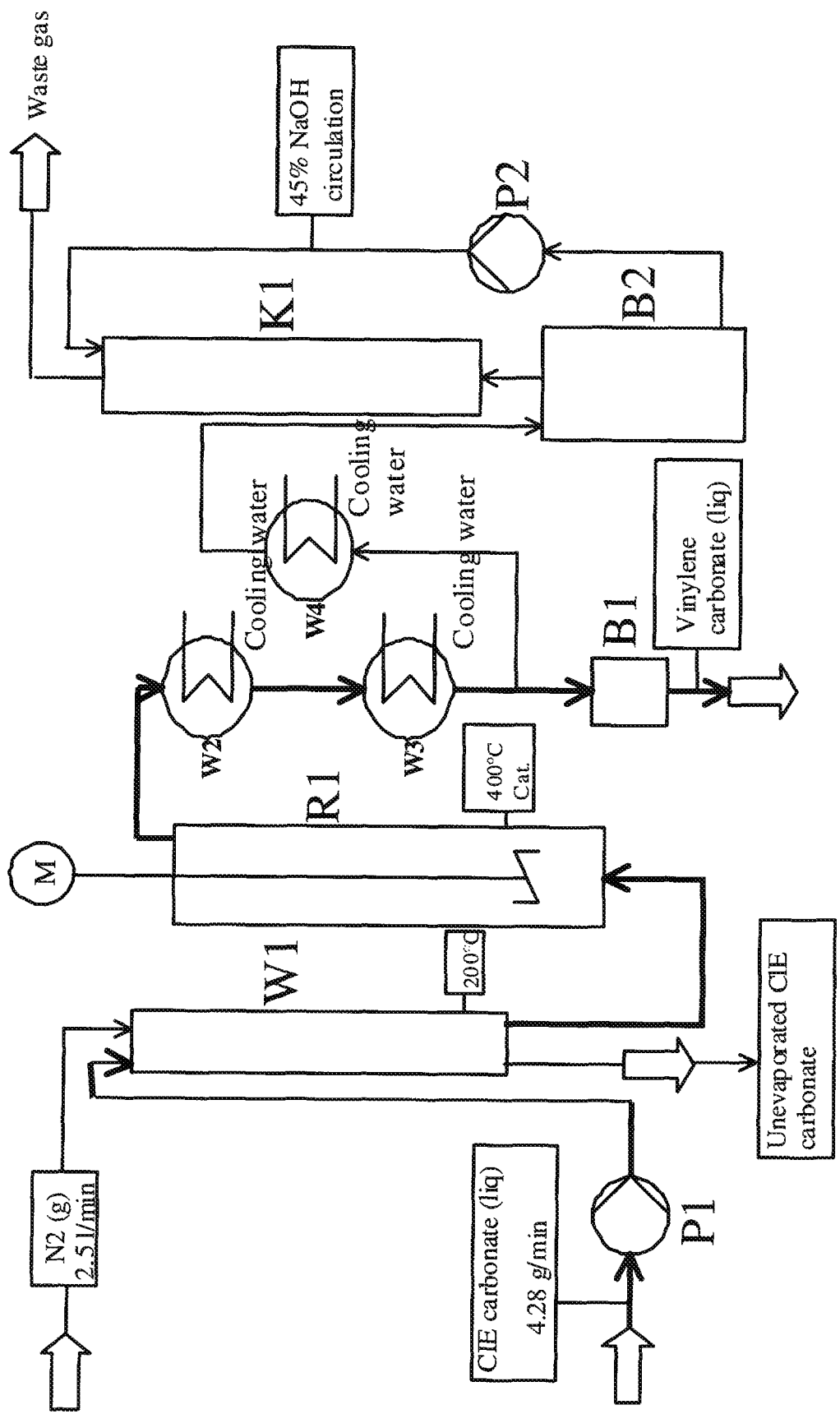

PROCESS FOR PRODUCING VINYLENE CARBONATE

The present invention relates to the industrial production of vinylene carbonate (VC) by eliminating hydrogen chloride from chloroethylene glycol carbonate (CGC) over solid catalysts in the gas phase.

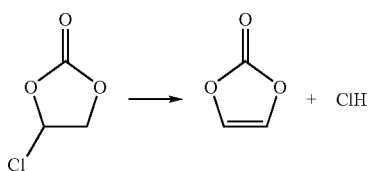

Vinylene carbonate is an important intermediate for the production of chemicals, pharmaceutical products, crop protection agents and in particular for polymers, paints and battery electrolytes.

Vinylene carbonate is produced by a known method by eliminating hydrogen chloride from chloroethylene glycol carbonate by means of tertiary amines, in particular triethylamine. The chloroethylene glycol carbonate is obtained by free radical chlorination of ethylene glycol carbonate by means of chlorine or sulphuryl chloride.

The synthesis was first published in 1953 by Newman and Addor (JACS, 1953, page 1263; JACS 1955, page 3789).

Ethylene glycol carbonate (GC) was photochlorinated in the absence of a solvent by means of ultraviolet light at 60-70° C., and the CGC formed was purified by vacuum distillation. Newman and Addor obtained VC by elimination by means of triethylamine in boiling ether, the mixture being heated overnight.

The isolation was effected by filtering off of the triethylammonium chloride and subsequent distillation, which gave a crude VC in 59% yield, which had to be purified by further distillation.

JP 2000/026449 describes the elimination in high-boiling solvents (b.p. 170-300° C.); explicitly, triethylamine is reacted in dibutyl carbonate for 20 hours at 50° C.

After the ammonium chloride has been filtered off and excess triethylamine distilled off, crude VC is isolated by simple distillation. In order to remove traces of amines, the VC is passed over a silica gel column. Finally, a purifying distillation is carried out. The chlorine content of the VC thus obtained is stated as 29 ppm, while comparative samples contain >3000 ppm. The yield is 56%.

DE-A 19 955 944 claimed the elimination of GC as solvent (b.p. 243-244° C.). CGC is initially introduced in GC and reacted in 1.5 hours by addition of triethylamine at 60° C. After excess triethylamine has been distilled off at 40° C. and evaporation has been effected over a thin-film evaporator at 100° C., a colourless mixture of VC and GC is obtained in 73% yield. No information is given about the purity.

The reactions of CGC in the liquid phase all suffer from the decomposability of VC, which is discussed explicitly in DE 199 55 944 A1. Accordingly, it decomposes in hours above 60° C. and in minutes above 80° C. The resulting polymers make it more difficult to filter off the salts with suction, and the exothermic decomposition makes the scale-up of such processes problematic.

In JOC, 1960, page 1042, Johnson and Patton describe the reaction of CGC over solid beds of CaSO4 catalysts in the gas phase at 250° C. and 50-60 mmHg.

The catalysts are very rapidly deactivated and at best achieve a conversion of 35-40% at selectivity of 40-45%. Higher or lower temperatures lead to a lower conversion. The catalysts can be regenerated by burning off.

Granulated active carbon and granulated activated alumina give only gaseous products. DE-A 1 135 452 describes the HCl elimination from CGC at 300-400° C. The CGC is passed in gaseous form over an inert support material which is coated with elements of subgroup I., II. or VIII of the Periodic Table of the Elements or salts or oxides thereof. The chlorides of iron, of cobalt and of copper are preferably used, particularly preferably cadmium chloride. Suitable support materials are pumice and silicates having particle sizes of 4 to 8 mm.

The catalysts are operated as a stationary bed at atmospheric pressure or reduced pressure and a temperature of 270 to 450° C., preferably of 300-400° C.

The behaviour of $CdCl_2$ on pumice is explicitly described. The catalyst is substantially more stable with about 270 hours and, at 74%, more selective than the $CaSO_4$ catalysts.

The space velocity was 0.15 kg of CGC per 1 of catalyst per hour and the inert gas stream was between 27 and 671 per kg of CGC. The average conversion was 87%.

The catalyst can be burned off at 500 to 700° C. with air.

The low conversion in spite of a low space velocity and furthermore the use of toxic $CdCl_2$ are unsatisfactory in the gas-phase process. The support material pumice is very soft and mechanically sensitive. Particularly problematic with such a process, however, is that considerable deposits of carbon-rich compounds make it difficult to control the burn-off process to be carried out regularly. A scale-up to the industrial scale is therefore difficult and very risky. The stability of such catalysts over many regeneration cycles is likewise completely unknown.

It is therefore an object of the invention to provide a gas-phase process which gives higher conversions and selectivities and permits safe and easy handling of all operating states on an industrial scale at higher space velocities and optionally a smaller inert gas stream, toxic heavy metals such as Cd being avoided as far as possible.

The fact that several publications on the wet chemical elimination with triethylamine have appeared since 1953 but only the article by Johnson and Patton of 1960 and DE-A-1 135 452 of 1961 exist with regard to the gas-phase elimination indicates that the difficulties of the elimination of HCl from CGC in the gas phase of heterogeneous catalysts were considered to be insurmountable among those skilled in the art.

Surprisingly, it was found that the process properties sought are achieved if catalyst beds agitated by thorough mixing or fluidized beds are employed. Zinc chloride is particularly suitable as an active component on inert support material, which is surprising, since zinc chloride melts at as low as 290° C.

The invention relates to a process for the production of vinylene carbonate by elimination of hydrogen chloride from chloroethylene glycol carbonate (CGC) over solid catalysts in the gas phase, characterized in that the reaction is optionally carried out under inert gas over catalyst beds agitated by thorough mixing, preferably over fluidized catalysts in so-called fluidized beds. A stirred fluidized bed is particularly preferred.

The process according to the invention can be carried out in various reactor types, for example reactors having thoroughly mixed catalyst beds, such as paddle dryers, rotary kilns, preferably having a bubble-forming, turbulent or flow-through fluidized bed, internally or externally circulating fluidized beds, fluidized beds having moving internals or additional bubble dividers, reactors having mechanical or additional agitation of the bed, for example by sound or knockers/vibrations, such as, for example, sound or ultrasound. It is preferably carried out in a stirred bubble-forming fluidized bed.

Suitable optionally used inert gases are all gases which do not react with the starting material or product under the chosen reaction conditions; particularly suitable inert gases are noble gases, such as argon, helium or neon, nitrogen, carbon monoxide or carbon dioxide or hydrogen halide compounds such as HCl. Preferably used inert gases are gases from the group consisting of helium, neon, argon, carbon monoxide and carbon dioxide. It is possible to carry out the process according to the invention with addition of an inert gas or of a mixture of a plurality of inert gases in any desired combination. It is also possible completely to dispense with a carrier gas.

The temperature can be varied in the temperature range from 300° C. to 600° C. The advantageous temperature range is between 350° C. and 500° C. A reaction temperature of 380° C. to 430° C. is preferred.

For the process according to the invention solid particles of the catalyst are introduced into the reaction space. The particles form a fixed bed into which the gas fed in flows. The inflow velocity of the gas fed in can be adjusted so that the fixed bed is fluidized and a fluidized bed forms. The corresponding procedure is known per se to the person skilled in the art. For this purpose, the inflow velocity of the gas fed in must correspond at least to the loosening velocity (minimum fluidization velocity). Loosening velocity is understood as meaning the velocity at which a gas flows through a bed of particles and below which the fixed bed is retained, i.e. below which the bed particles remain substantially stationary. Above this velocity, the fluidization of the bed begins, i.e. the bed particles move and initial bubbles form. During operation of a bubble-forming fluidized bed, the gas velocity is chosen so that it corresponds to one to fifty times the loosening velocity, preferably one to forty times, particularly preferably one to thirty times.

The solid catalyst consists of an inert support material with applied metals of subgroup I. or II. or of group VIII. of the Periodic Table of the Elements or salts or oxides thereof, consists; chlorides are preferably used, particularly preferably zinc chloride.

Silicates having a low BET surface area in the range smaller 10, preferably smaller 1, particularly preferably smaller 0.1 m$^2$/g are suitable as support material, preferably porous or rough glasses.

Furthermore, the solid catalyst may consist completely of salts or oxides of the metals of subgroup I. or II. or of group VIII. of the Periodic Table of the Elements without support material; oxides and/or chlorides are preferably used, particularly preferably zinc oxide and/or zinc chloride.

Deactivated catalyst can be regenerated by burning off with air or mixtures of oxygen and inert gas at temperatures between 300 and 700° C., preferably between 400 and 600° C.

Lost active components can be replaced by impregnation or spraying on of aqueous solutions of the salts.

Separating off finely divided solid discharge from the gas stream leaving the reactor can be effected, for example, by means of a cyclone, a filter or a gas scrubber. Separating off by means of a cyclone and/or a filter is preferred. The material separated off can be recycled directly into the bed by suitable recycling or can be collected separately from the material.

Below, the process according to the invention is illustrated with reference to some examples, but the examples are not to be understood as limiting the concept of the invention.

EXAMPLE

Example 1

Catalyst Preparation for Tubular Reactor 2 l=1052 g of a porous silica support having a sphere size between 1 and 2 mm were agitated with 400 ml of impregnating liquid at room temperature until all impregnating liquid had been absorbed.

The impregnating liquid consisted of 80 g of zinc chloride and water.

Thereafter, the catalyst was dried at 110° C. in a drying oven and finally calcined at 400° C. for 3 h.

The support material had an apparent density of 1.06 g/ml. Hg porosimetry gave a penetrated volume of 524 mm$^3$/g. The porosity was thus about 56%. The BET surface area, measured by nitrogen adsorption at −196° C., was <0.05 m$^2$/g. The specific surface area calculated from the Hg distribution was about 0.4 m$^2$/g.

The surface composition, determined by XPS, was, stated in atom %, was 5.2% of Mg, 11% of Na, 1.9% of F, 54.6%, 54.6% of O, 1.3% of Cl and 26% of Si. The volume contained 3.1% of Mg, 11.5% of Na, 1.1% of F, 53.4% of O, 2.9% of Ca, 1% of Cl and 27% of Si.

Example 2

Catalyst Preparation for Fluidized-Bed Reactor

The support described in Example 1 was comminuted in a Frewitt sieve and the fraction 0.315-0.16 mm was separated off using a sieve analysis machine.

1250 ml=1029 g were agitated with 597 ml of impregnating liquid consisting of 50 g of zinc chloride and water at room temperature until all impregnating liquid had been absorbed.

Drying was then effected for 24 h at 110° C. and 200 mbar.

Example 3

Fluidized Bed Experiment

The apparatus is shown in FIG. 1.

A Quartz glass reactor (R1) which has an internal diameter of 50 mm and a height of 700 mm was used for carrying out the experiment. A centrally mounted paddle stirrer with offset paddles at a height of 150 mm was present in the reactor. The stirrer is sealed from the atmosphere by means of a gland. The fluidized bed is brought to reaction temperature and kept at said temperature by means of external electrical heating. A stream of chloroethylene glycol carbonate that was vaporized in a gentle manner in an upstream evaporator (W1) after feeding via a pump in a stream of nitrogen was into the reactor. The gas emerging from the reactor was condensed by cooling, and the samples taken every 30 minutes from the collecting container (B1) were analysed by gas chromatography. The waste gas is scrubbed HCl-free with the aid of an alkaline scrubber (B2). The starting material chloroethylene glycol carbonate was added at about 4 g·min$^{-1}$. In addition, an inert gas stream of 2.5 l·min$^{-1}$ was introduced into the reactor. 180 g of a catalyst impregnated with ZnCl$_2$ as described in abovementioned Example 2 were present in the reactor. The mean particle size determined by laser diffraction was 126 µm. Complete conversion were initially observed. The secondary components detected by gas chromatography were substantially acetic acid and chloroacetaldehyde, and the main product was VC. The conversion was stable for several hours and then decreased slowly as a result of coking of the catalyst. The variation of the conversion and the selectivities with respect to the by products is listed in Table 1 below.

TABLE 1

Variation of conversion and by product selectivity

| Time, h | Conversion, % | S (acetic acid), % | S (chloroacetaldehyde), % |
|---|---|---|---|
| 0.5 | 99.9 | 1.5 | 2.7 |
| 1 | 100.0 | 0.3 | 4.6 |
| 1.5 | 100.0 | 0.2 | 4.8 |
| 2 | 99.9 | 0.2 | 6.8 |
| 2.5 | 99.9 | 0.2 | 7.0 |
| 3 | 99.9 | 0.3 | 6.4 |
| 3.5 | 99.7 | 0.3 | 6.9 |
| 4 | 99.6 | 0.2 | 7.2 |
| 4.5 | 99.4 | 0.1 | 9.3 |
| 5 | 98.9 | 0.1 | 11.8 |
| 5.5 | 98.5 | 0.1 | 12.2 |
| 6 | 98.1 | 0.1 | 12.3 |
| 6.5 | 97.3 | 0.2 | 13.0 |

The catalytic activity could be restored by burning off with air. Owing to the thorough mixing in the fluidized bed, hot spots which are known to the person skilled in the art as a major problem in the thermal oxidative regeneration of the coked catalysts did not form here. The temperature jumps here can easily reach several 100° C. damage reactor and catalyst. Owing to the chosen reaction procedure, this strong local overheating can be avoided. During the regeneration with the aid of air, the initially introduced bed warmed up only moderately by not more than about 25° C.

The average yield of VC, based on CGC used, is about 80% of theory.

COMPARATIVE EXAMPLE

Tubular Reactor, Fixed Bed

The experimental setup corresponded to that outlined in FIG. XX (1?). with the difference that the fluidized-bed reactor was replaced by a tubular reactor having a stationary catalyst bed. The reactor tube was about 2 m long and electrically thermostated and had an internal diameter of 40 mm. 2300 ml=1180 g of catalyst, prepared as described in Example 1, were introduced. The catalyst bed had a height of about 183 cm.

6 thermocouples which permit monitoring of the internal temperature were mounted along the bed axis.

In a nitrogen stream, the reactor was heated to 400° C. and the CGC metering into the evaporator was started.

The catalyst is loaded with 1000 g of CGC per hour, evaporated in a nitrogen stream of 50-60 l(S.T.P.)/h.

TABLE 2

Variation of conversion and by product selectivity

| Time, h | Conversion, % | S (acetic acid), % | S (chloroacetaldehyde), % |
|---|---|---|---|
| 2 | 100.0 | 0.1 | 10.3 |
| 10 | 100.0 | 0.1 | 16.0 |

TABLE 2-continued

Variation of conversion and by product selectivity

| Time, h | Conversion, % | S (acetic acid), % | S (chloroacetaldehyde), % |
|---|---|---|---|
| 20 | 99.9 | 0.2 | 17.8 |
| 30 | 99.8 | 0.2 | 16.8 |
| 50 | 99.2 | 0.2 | 17.3 |

The temperature variation in the reactor tube and the reduction of the conversion after 50 hours showed that the catalyst bed had to be regenerated.

At this point in time, VC had been obtained in an average yield of 69% of theory.

For regeneration, the metering of starting material was stopped and a gas mixture comprising 30 l(S.T.P.) of air and 60 l(S.T.P.) of nitrogen was passed per hour over the catalyst. After burning off for 3 hours, the amount of air was increased to 60 l(S.T.P.).

After 50 minutes the catalyst temperature at the penultimate thermocouple increased suddenly from 400 to 480° C. with a rising trend, whereupon the air supply was briefly stopped and, after the catalyst temperature had normalized, the amount of air was set again at 30 l(S.T.P.)/h.

After burning off for a further 13 h, the amount of air was increased again to 60 l(S.T.P.)/h, whereupon a 511° C. hot spot was indicated after a short time in the front part of the catalyst bed, at the $3^{rd}$ measuring point.

The air supply was briefly stopped again and further burning off was then effected for 4 h at 30 l(S.T.P.) and 9 h at 40 l(S.T.P.). The hot spot suddenly formed at the $2^{nd}$ measuring point and was prevented from causing a further increase in the temperature by shutting off the air.

After a further 9 h at 30 l(S.T.P.)/h, 40 l(S.T.P.) of air was set with the assumption that the predominant part of the deposits had now been burned off, and the additional nitrogen stream was shut off.

After burning off for 2.5 h in a pure air stream, a hot spot of 711° C. suddenly formed at the $1^{st}$ temperature measuring point and was controlled by immediately changing over to pure nitrogen.

The catalyst was burned off for a further 3 hours with 200 l(S.T.P.) of air with intensive observation. CGC in a hot nitrogen stream was then again passed over the catalyst, as described above.

The total duration of regeneration was 45 hours.

The catalyst once again showed the former activity; in the next runs burning off was effected after only 24 h so that not so many carbon-rich deposits settle on the catalyst.

The nitrogen stream for regeneration was increased to up to 10 times.

The burning-off behaviour was substantially more stable as a result of these measures but a scale-up to the industrial scale appears to be risky.

The catalyst was operated in this way for 15 cycles with a production time of about 332 h and a regeneration time of 181 h.

The average yield of VC over the total process was stable at about 69% of theory.

The invention claimed is:
1. Process for the production of vinylene carbonate by eliminating hydrogen chloride from chloroethylene glycol carbonate (CGC) over solid catalysts in the gas phase, wherein the reaction is optionally carried out under inert gas at between 300 and 600° C. over catalyst beds agitated by thorough mixing and the catalyst beds consist of an inert support material with applied metals of subgroup Ib or IIb, or of group VIII of the Periodic Table of the Elements or salts or oxides thereof, or the catalyst beds consist of salts or oxides of metals of subgroup Ib or IIb, or of group VIII of the Periodic Table of the Elements.

2. Process according to claim 1, wherein the reaction is carried out at between 350 and 500° C.

3. Process according to claim 1, wherein the inert gas is a gas from the group consisting of helium, argon, neon, nitrogen, carbon monoxide and carbon dioxide.

4. Process according to claim 1, wherein the agitated catalyst bed is a fluidized contact catalyst in a fluidized bed.

5. Process according to claim 1, wherein the catalyst beds consist of chlorides of metals of subgroup Ib, IIb or VIII of the Periodic Table of the Elements.

6. Process according to claim 1, wherein the catalyst beds consist of zinc oxide and/or zinc chloride or of an inert support material with applied zinc oxide and/or zinc chloride.

7. Process for the production of vinylene carbonate by eliminating hydrogen chloride from chloroethylene glycol carbonate (CGC) over solid catalysts in the gas phase, wherein the reaction is optionally carried out under inert gas at between 300 and 600° C. over catalyst beds agitated by thorough mixing, wherein the catalyst beds consist of zinc oxide and/or zinc chloride or of an inert support material with applied zinc oxide and/or zinc chloride.

* * * * *